US00PP29092P2

(12) United States Plant Patent
Jambura et al.

(10) Patent No.: US PP29,092 P2
(45) Date of Patent: Mar. 13, 2018

(54) ***AESCULUS* TREE NAMED 'AARON1'**

(50) Latin Name: *Aesculus×bushii*
Varietal Denomination: Aaron1

(71) Applicants: JN Plant Selections, LLC, Milwaukee, WI (US); Johnson's Nursery, Inc., Menomonee Falls, WI (US)

(72) Inventors: Aaron Jambura, West Bend, WI (US); Michael D. Yanny, Milwaukee, WI (US)

(73) Assignees: JN PLANT SELECTIONS, LLC, Milwaukee, WI (US), part interest; JOHNSON'S NURSERY, INC., Menomonee Falls, WI (US), part interest ( * ) Notice: Subject to any disclaimer, the term of this patent is extended or adjusted under 35 U.S.C. 154(b) by 22 days.

(21) Appl. No.: 14/999,948

(22) Filed: Jul. 18, 2016

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Penny J. Aguirre

(57) ABSTRACT

A new cultivar of *Aesculus* named 'Aaron1', that is characterized by its large inflorescences that are pinkish red in color, its inflorescences that are borne upright and within the foliage, its good resistance to leaf scorch, its good cold hardiness, and its resistance to leaf blotch.

2 Drawing Sheets

Botanical classification: *Aesculus×bushii*.

Cultivar designation: 'Aaron1'.

The present invention relates to a new and distinct cultivar of *Aesculus×bushii* plant, botanically known as *Aesculus* 'Aaron1' and will be referred to hereafter by its cultivar name, 'Aaron1'. The new cultivar is a deciduous tree grown for use as a landscape plant.

'Aaron1' was discovered by one of the Inventors in the spring of 2003 as a chance seedling growing in a production block of *Aesculus glabra* seedlings at a nursery in Jackson, Wis. The exact parentage is unknown; however it is most likely a seedling resulting from the cross-pollination of unnamed and unpatented plants of *Aesculus glabra* and *Aesculus pavia* (*Aesculus×bushii*) based on their characteristics and the origin of the seed.

Asexual propagation of the new cultivar was first accomplished by side veneer grafting onto a *Aesculus glabra* seedling under the direction of one of the Inventors in July of 2003 in Menomonee Falls, Wis. Asexual propagation by side veneer grafting and cleft grafting onto *Aesculus glabra* seedlings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Aaron1' as a unique cultivar of *Aesculus*.

1. 'Aaron1' exhibits large inflorescences that are pinkish red in color.
2. 'Aaron1' exhibits good resistance to leaf scorch.
3. 'Aaron1' exhibits good cold hardiness for an *Aesculus* with pinkish red flowers.
4. 'Aaron1' exhibits good resistance to leaf blotch.

A probably parent plant of 'Aaron1', an unnamed plant of *Aesculus glabra*, differs from 'Aaron1' in having flowers that are light yellow in color and in being taller in overall height. The probable parent plant of 'Aaron1', an unnamed plant of *Aesculus pavia*, differs from 'Aaron1' in having flowers that are bright red in color and in being less cold hardy. 'Aaron1' can be most closely compared to the *Aesculus×carnea* cultivars 'Ft. McNair' (not patented) and 'Briotii' (not patented). 'Ft. McNair' is similar to 'Aaron1' in having inflorescences that are pinkish red in color. 'Ft. McNair' differs from 'Aaron1', in having a more rounded plant habit, in being less cold hardy, and in having lower quality late season foliage due to leaf scorch and leaf blotch. 'Briotii' differs from 'Aaron1' in having inflorescences that are brighter red in color, in being less cold hardy, and in having lower quality late season foliage due to leaf scorch and leaf blotch.

BRIEF DESCRIPTION OF THE DRAWINGS

The accompanying colored photographs illustrate the overall appearance and distinct characteristics of the new *Aesculus*. The photographs were taken of a plant 12 years in age as field grown outdoors at a nursery in Menomonee Falls, Wis.

The photograph in FIG. 1 provides a side view of a plant of 'Aaron1' in bloom.

Figure 1:
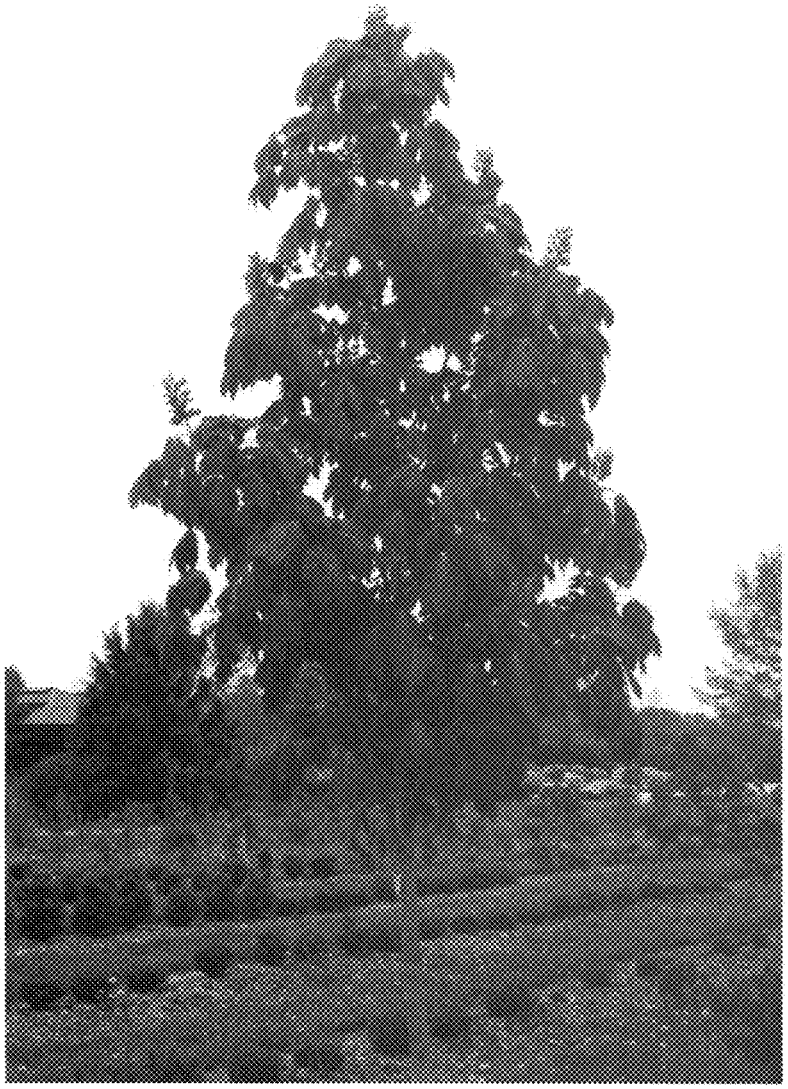
Figure 2:
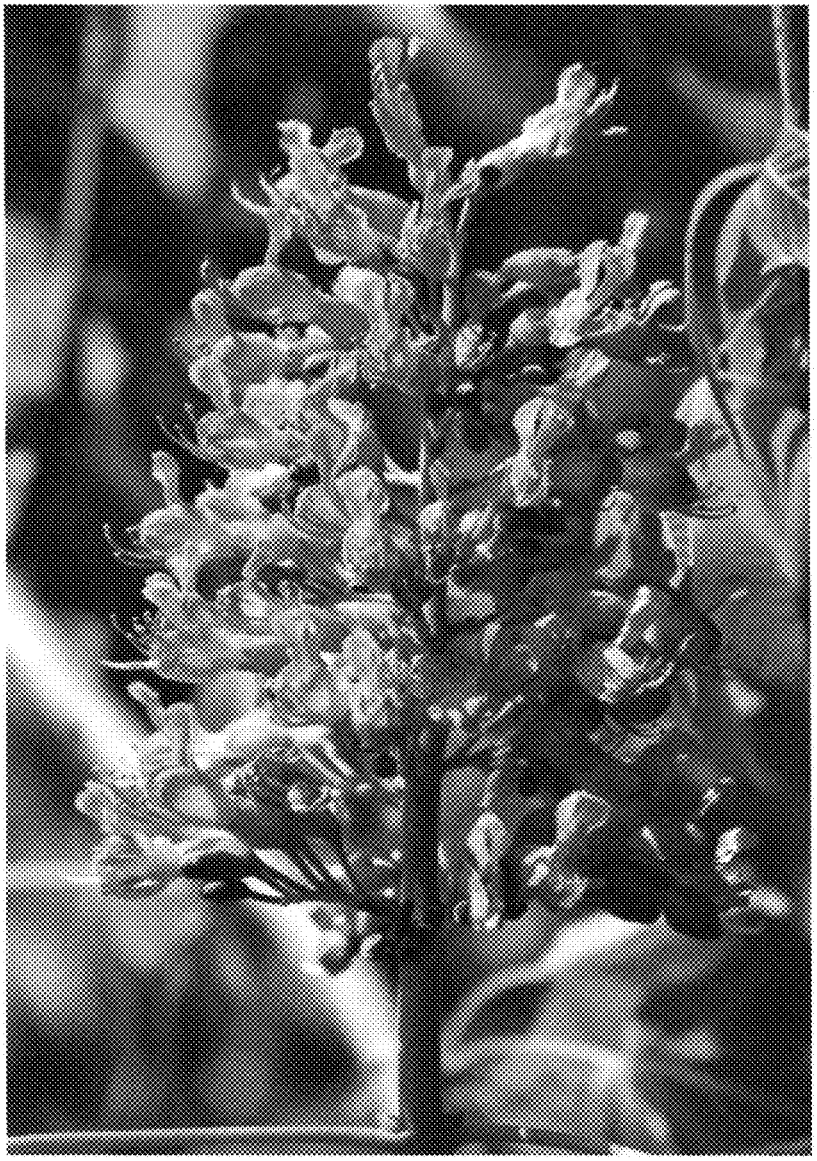

The photograph in FIG. 2 provides a close-up view of an inflorescence of 'Aaron1'.

The colors in the photographs are as close as possible with the photographic and printing technology utilized and the color values cited in the detailed botanical description accurately describe the colors of the new *Aesculus*.

DETAILED BOTANICAL DESCRIPTION OF THE PLANT

The following is a detailed description of 2 year-old plants of the new cultivar as grown outdoors in 2-gallon containers in a nursery in Menomonee Falls, Wis. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid-May in Jackson, Wis.

*Plant type*.—Deciduous tree.

*Plant habit*.—Upright with inflorescences that are borne upright.

*Height and spread*.—13 year-old plants reaches an average of 3.7 m in height and 0.9 m in width with a caliper of 6.35 cm.

*Cold hardiness*.—At least to U.S.D.A. Zone 5b.

*Diseases and pests*.—Resistance to leaf blotch (*Guignardia aesculi*) and leaf scorch (*Xylella fastidiosa*) has been observed.

*Root description*.—Woody taproot with lateral woody roots, color similar to mature branch color.

*Propagation*.—Cleft grafting and side veneer grafting on *Aesculus glabra* seedlings.

*Propagation time*.—New grafts made in late winter take about one month for a terminal bud to emerge and until the end of the growing season to produce a young tree about 8-inches in height that is ready for transplant.

*Growth rate*.—Slow to moderate.

Branch description:

*Branch habit*.—2 lateral branches and 1 to 2 secondary branches per lateral branch.

*Branch size*.—Main stem; an average of 8 cm in length (above the graft) and 1 cm in width measure 8 cm from the graft, lateral branches; an average of 50 cm in length and 8 mm in width, secondary; up to 30 cm in length and 6 mm in width.

*Branch shape*.—Oval.

*Branch color*.—Twigs (first year growth); 144A, lateral branches and main stems: a blend of 198B and 200B.

*Branch surface*.—Twigs; very minute and sparse pubescence (appearance is smooth) with lenticels oval in shape, <0.5 mm in length, about 8 per stem 1 cm in length, 156D in color, 2nd year wood; relatively smooth barked with lenticels round in shape, <0.5 mm in length, about 10 per 1 cm of branch, and 199D in color, main stem; slightly fissured bark.

*Internode length*.—Average of 4.5 cm.

Foliage description:

*Leaf shape*.—Fan-shaped in overall outline.

*Leaf division*.—5 to 7 palmate.

*Leaf size*.—Average of 20 cm in length and 23 cm width.

*Leaf quantity*.—Average of 17 per stem 35 cm in length.

*Leaflet shape*.—Oblanceolate.

*Leaflet base*.—Attenuate.

*Leaflet apex*.—Acuminate.

*Leaflet venation*.—Pinnate pattern, conspicuous especially on lower surface, color on upper surface 144C, color on lower surface 145C.

*Leaflet margins*.—Serrulate.

*Leaf attachment*.—Petiolate.

*Leaf arrangement*.—Opposite.

*Leaflet surface*.—Glabrous and dull on upper surface and glabrous and satiny on lower surface.

*Leaflet color*.—Newly expanded and mature upper and surface 137A, newly expanded and mature 137B, no unique fall color.

*Leaflet size*.—Up to 16 cm in length and 5.5 cm in width.

*Petioles*.—Up to 15 cm in length and an average of 3 mm in width, clasping to stem at base, 144B in color with base slightly suffused with 176B , surface is glabrous and satiny, held horizontal to a 45° angle to branch, slightly pendant, moderate strength.

*Stipules*.—None.

*Leaf buds*.—<0.5 mm in length, imbricate, triangular in shape, N119C.

Flower description:

*Inflorescence type*.—Terminal panicles of pea-like flowers on main and secondary branches, blooms from the base to the apex, flowers radially and uniformly dispersed around the inflorescences.

*Inflorescence size*.—An average of 9 cm in length and 7 cm in width.

*Lastingness of inflorescence*.—About 2 weeks.

*Flower size*.—An average of 2.5 cm in depth and about 2 cm in diameter.

*Flower fragrance*.—None.

*Flower/bud number per inflorescence*.—An average of 76 open flowers and buds.

*Peduncle*.—Round in shape, an average of 5 mm in length and 2 mm in width, 144A in color, surface is glabrous, strong in strength.

*Petiole*.—Round in shape, up to an average of 1 cm in length and 1 mm in width, color is a blend of 181A and 161A, glabrous surface, moderately strong in strength.

*Flower buds*.—Oblong in shape, an average of 1 cm in length and 5 mm in width, petal portion is 183A in color, calyx portion a blend of 145A and 178B.

*Flower type*.—Papilionaceous, held at an average angle of 60° (90°=upright).

*Calyx*.—Campanulate shaped, tubular, an average of 1 cm in length and 5 mm in width, 100% fused around an open flower, 5 tips enclosed around flower petals, tips; an average of 3 mm in length and 2 mm in width, obtuse apexes, surface is glabrous and shiny, color is a blend of 181A and 161A, small spot on the edge of each tip 185B.

*Sepals*.—5, fused base, acute apex, entire margins, an average of 1 cm in length and 2 mm in width, obtuse to triangular in shape, outer surface is glabrous and shiny, inner surface is glabrous, outer color is a blend of 181A and 161A, small spot on the edge of each tip 185B, inner color is mostly 160A and occasionally tinted with 181B.

*Petals*.—4, 50% fused into calyx, 2 bottom petals; 2 cm in length, bottom to middle section is 2 mm in width, top section is 5 mm in width, undulate margins, rounded apex, upper and lower surfaces; shiny, satiny and moderately covered with puberulent hairs on the margins that match the surface color and are less than 0.5 mm in length, color: upper and lower surface when opening; mostly 150A, tips a blend of 150A and 182A, upper surface when fully open; base to mid section is 11B, mid section to apex is 182A to 182B with spots of 154A, moderately covered with pollen in the mid section 23A, lower surface when fully open; base to mid section is 155B, mid section to apex a blend of 182B and 155B with spots of 154A, 2 outer petals; 1.5 cm in length, 1 cm in width, undulate margins, bluntly acute apex, upper and lower surfaces; shiny, satiny and moderately covered with puberulent hairs on the margins that match the surface color and are less than 0.5 mm in length, color: upper and lower surface when opening; a blend of 150A and 182A, upper and lower surface when fully open; base to mid section is 11B, mid section to apex is 182A to 182B with spots of 154A.

*Receptacle*.—An average of 2 mm in depth, 3 mm in width, glossy surface, 150A in color.

Reproductive organs:

*Gynoecium*.—Pistil; 1, an average of 2.2 cm in length and 1 mm in width, semi-glossy and covered with woolly puberulent hairs matching surface color and less than 0.5 mm in length, style; 29D in color and 2.1 cm in length, stigma; minute, 181A in color, ovary; superior, dull surface, 18C in color, 2 mm in length and width.

*Androcoecium*.—Stamens; 7, 2 cm in length and 1 mm in width, filament; 1.9 mm in length, 1 mm in width, blended color; base to mid section color is NN155B, midsection to tip color is 180C, semi-glossy and covered with woolly puberulent hairs matching surface color and less than 0.5 mm in length, dorsifixed anther; club shaped, 1 mm in length and width and N170A in color, pollen is moderate in quantity and located mostly on the bottom 2 petals, 23A in color.

*Fruit and seed*.—Capsule, average of 2 develop per inflorescence, oval-rounded in shape, an average of 1.7 cm in length and 1.2 cm in width, 146D in color, spikey surface with spikes an average of 0.5 mm in length, triangular in shape, and 145C in color with tip 166B, seed; nut, an average of 8 mm in length and width, 166B in color with flesh 155A, glossy surface.

It is claimed:

1. A new and distinct cultivar of *Aesculus* plant named 'Aaron1' as herein illustrated and described.

* * * * *